United States Patent
Jonsson et al.

(10) Patent No.: US 11,000,606 B1
(45) Date of Patent: May 11, 2021

(54) DISINFECTION DEVICE

(71) Applicant: Sotspor, LLC, Rancho Santa Margarita, CA (US)

(72) Inventors: Karl S. Jonsson, Rancho Santa Margarita, CA (US); Arman Victor Bastani, Santa Ana, CA (US)

( * ) Notice: Subject to any disclaimer, the term of this patent is extended or adjusted under 35 U.S.C. 154(b) by 0 days.

(21) Appl. No.: 17/148,856

(22) Filed: Jan. 14, 2021

(51) Int. Cl.
*A61L 2/10* (2006.01)
*A61L 2/00* (2006.01)
*A61L 2/26* (2006.01)

(52) U.S. Cl.
CPC .......... *A61L 2/0047* (2013.01); *A61L 2/26* (2013.01); *A61L 2202/11* (2013.01); *A61L 2202/14* (2013.01); *A61L 2202/24* (2013.01)

(58) Field of Classification Search
CPC ...... A61L 2/0047; A61L 2/26; A61L 2202/11; A61L 2202/14; A61L 2202/24; A61L 2/10; A61L 2/24; A61L 9/20; A61L 2/084; A61L 2209/12; A61L 2202/25; A61L 2209/111; A23L 3/28; A23V 2002/00; F21V 33/0044; F21V 33/0064; F21V 23/003; F21V 23/04; F21V 3/06; F21V 33/0068; F21V 23/0471; F21S 8/03; F21W 2131/205; F21W 2131/208; F21Y 2113/00; F21Y 2115/10
See application file for complete search history.

(56) References Cited

U.S. PATENT DOCUMENTS

| | | |
|---|---|---|
| 2008/0008620 A1 | 1/2008 | Alexiadis |
| 2016/0136312 A1 | 5/2016 | Park et al. |
| 2018/0320872 A1 | 11/2018 | Weeks et al. |
| 2019/0209722 A1 | 7/2019 | Stibich et al. |
| 2019/0224353 A1 | 7/2019 | Park et al. |
| 2020/0230271 A1* | 7/2020 | Choi ................ F21V 15/01 |

OTHER PUBLICATIONS

Crist, Ry, UVC wands kill viruses. Experts warn they're also a 'major safety issue', Oct. 20, 2020, Retrieved from https://www.cnet.com/news/uvc-light-wands-kill-viruses-experts-warn-major-safety-issue-coronavirus-covid-19/ on Nov. 12, 2020.

DiLaura, et al., Chapter 3: Photobiology and Nonvisual Effects of Optical Radiation, The Lighting Handbook Reference and Application, Tenth Edition, Published by the Illuminating Engineering Society, NY, NY, 2011, pp. 3.1-3.23.

IES Photobiology Committee, IES Committee Report: Germicidal Ultraviolet (GUV)—Frequently Asked Questions, IES CR-2-20-V1, ISBN 978-0-87995-389-8, May 7, 2020, Retrieved from https://media.ies.org/docs/standards/IES%20CR-2-20-V1a-20200507.pdf on Jan. 9, 2021.

(Continued)

*Primary Examiner* — Xiuyu Tai (74) *Attorney, Agent, or Firm* — Young's Patent Services; Bruce A Young (57) ABSTRACT

A lighting module includes a connector having a first contact and a second contact, a first device that emits ultraviolet (UV) light, and a second device that emits visible light. The UV light emitted by the first device is in a first wavelength range of 200-315 nm and the visible light emitted by the second device is in a second wavelength range of 400-750 nm. The first device emits substantially no light at a wavelength greater than 550 nm. Both the first device and the second device are coupled to the first contact. The lighting module may be used in a disinfection device.

22 Claims, 4 Drawing Sheets

(56) References Cited

OTHER PUBLICATIONS

IUVA, COVID-19 Applicable / Usable/Useful in Disinfecting N95 Respirators, Retrieved from https://uvsolutionsmag.com/buyersguide/services/0_N95Disinfect_COVID19 on Nov. 12, 2020.

IUVA, IUVA Fact Sheet on UV Disinfection for COVID-19, Retrieved from https://www.iuva.org/IUVA-Fact-Sheet-on-UV-Disinfection-for-COVID-19 on Nov. 12, 2020.

Klaran, Datasheet for Klaran® WD Series UVC LEDs, Oct. 10, 2020, Retrieved from https://www.klaran.com/images/Products/CIS_Klaran_WD_DS_101020.pdf on Jan. 9, 2021.

Kowalski, Walsh, and Petraltis, 2020 COVID-19 Coronavirus Ultraviolet Susceptibility, Mar. 12, 2020, Retrieved from https://www.monsolar.net/wp-content/uploads/2020/04/2020-COVID-19-Coronavirus-Ultraviolet-Susceptibility_marzo_2020.pdf on Jan. 10, 2021.

Lowe, John, et al., N95 Filtering Facepiece Respirator Ultraviolet Germicidal Irradiation (UVGI) Process for Decontamination and Reuse, Nebraska Medicine, Apr. 10, 2020, Retrieved from https://www.nebraskamed.com/sites/default/files/documents/covid-19/n-95-decon-process.pdf on Nov. 12, 2020.

Targus, Targus® Named CES® 2021 Innovation Awards Honoree for its UV-C LED Disinfection Light, Dec. 15, 2020, Retrieved from https://us.targus.com/blogs/press-room/strong-targus-named-ces-2021-innovation-awards-honoree-for-its-uv-c-led-disinfection-light on Dec. 16, 2020.

UL, Ultraviolet-C (UVC) germicidal devices: what consumers need to know, Jul. 30, 2020, Retrieved from https://collateral-library-production.s3.amazonaws.com/uploads/asset_file/attachment/26057/CT_26219573_UVC-Germicidal-Devices-flyer_digital_FINAL_073020.pdf on Nov. 12, 2020.

US Food and Drug Administration, UV Lights and Lamps: Ultraviolet-C Radiation, Disinfection, and Coronavirus, Aug. 19, 2020, Retrieved from https://www.fda.gov/medical-devices/coronavirus-covid-19-and-medical-devices/uv-lights-and-lamps-ultraviolet-c-radiation-disinfection-and-coronavirus on Nov. 12, 2020.

* cited by examiner

DISINFECTION DEVICE

TECHNICAL FIELD

The present subject matter relates to a device that uses ultraviolet (UV) light, more specifically UV-C light, for disinfection.

BACKGROUND

Ultraviolet (UV) light, which is invisible to the naked eye, is well known to kill bacteria and viruses, especially UV-C band light having a wavelength of between 200 and 280 nanometers (nm). Many devices are commercially available that emit UV light to disinfect a surface, but UV light can be harmful to humans, causing irritation or burns of eyes and skin. This is especially an issue for light in the UV-B band (wavelengths between 280 and 315 nm). Many germicidal UV sources, such as UV mercury lamps and xenon arc lamps provide a wide spectrum of light ranging from UV-C(or even shorter wavelengths) through the UV-B and UV-A bands into the visible spectrum. Light emitting diodes (LEDs) are now available that emit UV light in a narrow wavelength band of less than 50 nm centered in the upper UV-C band, such as 265 nm, so that little UV-B and substantially no UV-A or visible light is emitted. Thus, while it can be easy to tell using the naked eye whether a traditional germicidal UV source is on, this is not the case for disinfecting devices using UV-C LEDs.

BRIEF DESCRIPTION OF THE DRAWINGS

The accompanying drawings, which are incorporated in and constitute part of the specification, illustrate various embodiments. Together with the general description, the drawings serve to explain various principles. In the drawings.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures and components have been described at a relatively high-level, without detail, in order to avoid unnecessarily obscuring aspects of the present concepts. A number of descriptive terms and phrases are used in describing the various embodiments of this disclosure. These descriptive terms and phrases are used to convey a generally agreed upon meaning to those skilled in the art unless a different definition is given in this specification Some descriptive terms and phrases are presented in the following paragraphs for clarity.

Ultraviolet (UV) light refers to electromagnetic radiation having a wavelength between about 100 and about 400 nm. Although not all sources agree on exact definitions, as the terms are used herein, UV-C light refers to electromagnetic radiation having a wavelength between 200 and 280 nanometers (nm), UV-B light refers to electromagnetic radiation having a wavelength between 280 and 315 nm, and UV-A light refers to electromagnetic radiation having a wavelength between 315 and 400 nm. UV light, including UV-A, UV-B, and UV-C light, is invisible to most humans although some people, especially children and young adults, may be able to perceive some UV-A light.

Visible light refers to electromagnetic radiation having a wavelength between about 400 nm and about 750 nm, depending on the individual viewer. Although not all sources agree on exact wavelengths to represent colors, as the terms are used herein, violet light has a wavelength of below about 450 nm and may overlap with the lower end (i.e. longer wavelengths) of the UV-A band, blue light has a wavelength between about 450 nm and 485 nm, cyan light has a wavelength between about 485 nm and 500 nm, green light has a wavelength between about 500 nm and 565 nm, yellow light has a wavelength between about 565 nm and 590 nm, orange light has a wavelength between about 590 nm and 625 nm, and red light has a wavelength above 625 nm.

Germicidal UV (GUV) lights are available from a variety of sources. The Illuminating Engineering Society (IES) created a report entitled "IES Committee Report: Germicidal Ultraviolet (GUV)—Frequently Asked Questions" (IES CR-2-20-V1, ISBN 978-0-87995-389-8), which is incorporated by reference in its entirety herein for any and all purposes, that discusses some of the issues related to the use of GUV lights with focus on their use for inactivating the SARS-CoV-2 virus which caused the COVID-19 pandemic. Their safety, however, has been a concern. Underwriters Laboratories (UL) issued a warning flyer about the use of GUV lamps by consumers entitled "Ultraviolet-C(UVC) germicidal devices: what consumers need to know" on Jul. 30, 2020, which is incorporated by reference in its entirety herein for any and all purposes.

The US Food and Drug Administration (FDA) has jurisdiction over medial products that emit radiation, including those that emit UV light, that are intended for medical purposes, such as products that disinfect other medical devices, under section 201(h) of the Federal Food, Drug, and Cosmetic Act, and therefore can require FDA clearance, and therefore, such devices may require approval, or authorization, prior to marketing. Certain GUV lights, such as some of the embodiments described herein, may be subject to FDA approval for COVID-19-related applications, including emergency use authorization, while the full FDA authorization process is underway.

Studies have shown that bacteria and viruses can have their DNA disrupted by certain wavelengths of UV light, thus killing the bacteria and inactivating the viruses (which are not technically "alive" to start with). The specific wavelength that is most effective varies somewhat depending on the specific bacteria/virus being targeted, but UV-C light having a wavelength of about 265 nm is generally deemed most effective for a broad range of pathogens, although any UV light in a wavelength range of about 200 nm to 315 nm can have some effectiveness. Table 3.4 in section 3.6 of the IES publication "The Lighting Handbook, $10^{th}$ Edition" (Chapter 3 of The Lighting Handbook $10^{th}$ Edition, ISBN 978-087995-241-9, entitled "Photobiology and Nonvisual Effects of Optical Radiation" is incorporated by reference in its entirely herein for any and all purposes) presents the relative effectiveness of different wavelengths of UV light in killing a common strain of *E. coli*. This table uses the effectiveness of UV light with a wavelength of 265 nm as its 100% effective reference point and shows decreasing effectiveness as the wavelength increases or decreases from 265 nm. Using the IES data and extrapolating between data points shows that wavelengths of about 259 nm and 270 nm are 95% as effective as 265 nm UV light, wavelengths of about 254 nm and 274 nm are 85% as effective as 265 nm UV light, wavelengths of about 250 nm and 278 nm are 75% as effective as 265 nm UV light, wavelengths of about 241 nm and 288 nm are 50% as effective as 265 nm UV light, and wavelengths of about 235 nm and 294 nm are about one third as effective as 265 nm UV light.

Early studies have shown that UV-C light can be effective against the SARS-CoV-2 virus, and although no definitive data could be found showing which exact wavelength is most effective for that virus, the effectiveness curve for *E. coli* described above is likely to be close to accurate for the SARS-CoV-2 virus as this has been true for many other pathogens. There is still work being performed to determine the dosage of UV light required to inactive the SARS-CoV-2 virus, but a paper by Kowalski, Walsh, and Petraltis entitled "2020 COVID-19 Coronavirus Ultraviolet Susceptibility" (available from www.researchgate.net), published on Mar. 12, 2020 and incorporated by reference in its entirety herein for any and all purposes, suggests that a dosage of 67 Joules/meter$^2$ (J/m$^2$), which is 6.7 milliJoules/centemeter$^2$ (mJ/cm$^2$), is enough to inactivate 90% of the SARS-CoV-2 virus on a surface, but this is rounded up to 10 mJ/cm$^2$ for use herein. So if a germicidally-effective UV-C light is provided at a power level of 10 mW/cm$^2$ on a surface contaminated with SARS-CoV-2 virus, it is expected that at least 90% of the virus would be deactivated after 1 second, 99% after 2 seconds, 99.9% after 3 seconds, and 99.99% after 4 seconds.

Because UV light, especially UV-B light, can be harmful to humans by causing irritation and even burns on a person's skin and eyes, care must be taken with GUV lights to ensure that there use does no harm to people as they are used to disinfect air or surfaces. Most GUV lights available today use mercury or xenon lamps that emit a broad spectrum of light from the UV-C range through UV-B, UV-A, and into the visible light spectrum, so that a person can tell if they are on and emitting UV light. Low-pressure mercury lamps, for example, emit most of their energy at 253.7 nm (UV-C) with their second highest output at 435.8 (violet), but they also have spectral output at 313.2 nm (UV-B), 365.0 nm (UV-A), 404.6 nm (violet), and 546.1 nm (green). This does not mean that they are safe on their own, however. The UL flyer referenced above states "UVC lamps have little visible light output, so our natural defensive reactions to optical hazards (blinking, squinting, or trying to look away) may not be triggered to protect us adequately."

Consumer-grade so-called GUV lamps using LEDs often have little to no light output at an effective wavelength between 200 and 315 nm but are simply "Black Lights" emitting a range of UV-A and visible violet light to provide an illusion of effectiveness. True UV-C LEDs are not yet available at consumer price-points, but as UV-C LEDs become more mainstream, they are likely to allow consumer-grade products to generate true UV-C light effective at killing bacteria and deactivating viruses. In addition, true medical-grade devices may also use UV-C LEDs to minimize size and power as compared to traditional GUV lamps. But UV-C LEDs have little to no UV-A or visible light output, so it may be very difficult to determine whether a GUV lamp using a UV-C LED is on and emitting UV light.

A lighting module that emits both germicidally-effective UV-C light and substantial amounts of visible light is disclosed herein. The lighting module can take on any form factor, including that of a standard light bulb to allow it to be used to retrofit existing devices, an LED strip light, or a custom form factor. The lighting module may be designed so that whenever the UV-C light is on, the visible light is active. Active, as the term is used herein, means that the light is either on and emitting a steady-state amount of light, or it is being actively modulated, such as by blinking the light (e.g. a strobe light), or by pulsing the light by ramping its intensity up and down over time. Thus, the visible light may not be on and emitting light at every instance that it is active as the visible light may be temporarily turned off as a part of the modulation.

Making the visible light active whenever the UV-C light is on allows the visible light to act as a warning that the UV-C light is on, even though the UV-C light cannot be seen. The visible light may be on at a steady-state level or may be modulated which may enhance its warning effect. The visible light may be bright enough, to attract the attention of a viewer, or even bright enough to cause a reflexive reaction to look away. If the visible light is modulated, the modulation rate may be fast enough to cause a feeling of urgency or warning and designed such that the visible light is not fully off for more than a few seconds or even not off for more than one second, or even less, to avoid an onlooker not noticing the visible light. The visible light may be any color, but a color often associated with a warning, such as yellow, orange, or red, may be used to more clearly convey the message that it may be dangerous to look at the light.

The lighting module may be incorporated into a disinfection device, or alternatively, the components of the lighting module as described may be fully integrated into a disinfection device. The disinfection device may be used as a medical device requiring FDA authorization, or it may be sold into industrial or consumer settings where FDA authorization may not be required but other certifications may be needed. At least one embodiment is targeted for use in an operating room to disinfect a surface that is suspected of being contaminated with the SARS-CoV-2 virus. The disinfection device can be designed to be effective at disinfecting surfaces or volumes of fluid (e.g. air or water). The visible light may be used as a warning, an indication of proper operation and not necessarily, or as an indication of where a germicidally-effective power level of UV light is available, or any combination thereof.

Reference now is made in detail to the examples illustrated in the accompanying drawings and discussed below.

Figure 1:
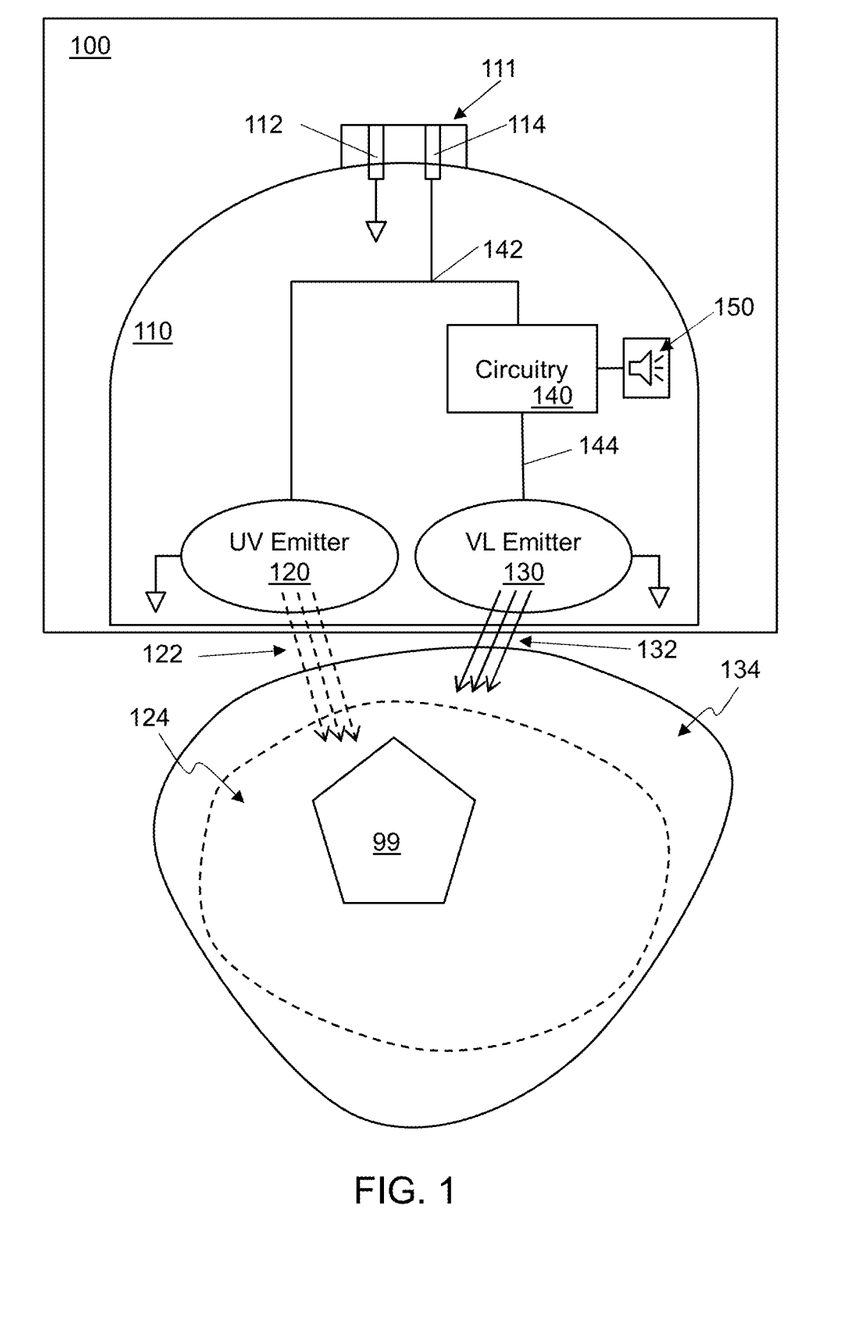
FIG. 1 shows a block diagram of an embodiment of a disinfection device.

FIG. 1 shows a block diagram of an embodiment of a disinfection device 100. The disinfection device 100 includes a lighting module 110 and may include other components, such as a power supply, switch, motion sensing cut-offs, fans, timers, or any other circuitry, as well as mechanical components such as structural elements, enclosures, mirrors, and lenses (which may be made from silica or quartz that is transmissive to both visible and UV light) that may be appropriate for an embodiment. Other embodiments may not have a separate lighting module 110 but may integrate some or all of the components of the lighting module 110 directly into the disinfection device 100.

The lighting module 110 includes a first device 120 that emits ultraviolet (UV) light 122 in a first wavelength range of 200-315 nanometer (nm) and substantially no light at a wavelength greater than 550 nm. The first device 120 is mounted within the disinfection device 100 to have a first exposure pattern 124 for the UV light 122. The first device 120 may be any type of device that emits UV light including, but not limited to, a low-pressure mercury bulb, a medium-pressure mercury bulb, a pulsed xenon arc lamp, one or more light emitting diodes (LEDs), a krypton-chlorine excimer lamp, or any combination of UV light emitters.

The UV light 122 in the first wavelength range is effective at killing or deactivating at least one pathogen, such as the SARS-CoV-2 virus or other corona viruses, rotaviruses, *streptococcus* bacteria, or *E. coli* bacteria and may, depending on the embodiment, be in a wavelength subrange of 241-288 nm. The first device 120 may include a light emitting diode (LED) having a peak emission in a wavelength subrange of 259-270 nm in at least some embodiments. An embodiment may use one or more WD Series UV-C LEDs from Klaran °, such as the KL265-50V-SM-WD LED (described in the Klaran WD Series UVC LEDs datasheet, published Oct. 10, 2020, which is incorporated by reference herein for any and all purposes and available from their website www.klaran.com), which has a 70 mW optical output with a forward voltage of about 8 Volts (V) and a forward current of 500 milli-Ampere (mA) with a peak emission of 265 nm±5 nm and an output the falls to less than 10% of peak output outside of a range of +10 nm to −15 nm about the peak output (i.e. nominally 250 nm to 275 nm). The first device 120 may, in some embodiments, emit the UV light 122 at a power level sufficient to deactivate at least 90% of SARS-CoV-2 virus on a surface of a medical device within one second at a distance of 0.5 meters or greater. This may equate to a power level of greater than 10 mW/cm$^2$ at a distance of 0.5 meters from the disinfecting device 100. If three 70 mW UVC LEDs are used as the first device 120, this power level might be achieved for an area of about 20 cm$^2$ if the LEDs are proper placed and the emitted UV light properly directed. Thus, the disinfection device 100 may be used to disinfect a surface 99 of an operating room that is suspected of being contaminated with the SARS-CoV-2 virus within the UV emission pattern 124.

The lighting module 110 also includes a second device 130 that emits visible light 132 in a second wavelength range of 400-750 nm. The second device 130 may include any type of light emitting device, depending on the embodiment, including, but not limited to, an incandescent bulb, a fluorescent bulb, or one or more LEDs. In some embodiments, the second device 130 may have a peak emission in a wavelength subrange of 565-750 nm to emit yellow, orange, or red visible light, indicating a hazardous condition. The emitted visible light 132 may be bright enough to encourage an observer to look away from the disinfection device 100. The second device 130 is mounted within the disinfection device 100 to have a visible light exposure pattern 134 for the visible light 132.

The relationship between the UV exposure pattern 124 and the visible light exposure pattern 134 may be different for different embodiments, depending on the application. In some embodiments, the visible light exposure pattern 134 completely covers (as shown in FIG. 1) and may be significantly larger than the UV exposure pattern 124 to present a keep-out area for an observer. This may be done when the power level of the UV is especially hazardous and it is important that a person avoid the UV exposure pattern 124 with any body part. In other embodiments, the visible light exposure pattern 134 is substantially the same as the UV exposure pattern 124. The phrase "substantially the same" in this case is meant to convey that an intersection of the areas of the UV exposure pattern 124 and the visible light exposure pattern 134 is about the same size as the union of the areas of the UV exposure pattern 124 and the visible light exposure pattern 134, such as the intersection is at least 75% of the size of the union, but that there may be areas that are within either one of the exposure patterns 124, 134, that are not within the other exposure pattern 132, 124. This may be done in embodiments where the intent is to present a general idea to a user what the UV exposure pattern 124 really is. In yet other embodiments the visible light exposure pattern 134 is a subset of the UV exposure pattern 124 and shows an area where a power level of the UV light 122 is germicidally effective. A germicidally-effective power level may vary depending on the application or the operating instructions for the disinfection device 100. So in one embodiment, a disinfection device 100 with operating instructions that indicate a surface to be disinfected by the UV light 122 should be kept in place for 3-4 seconds at a distance of 0.5 meters may have a visible light exposure area 134 that shows where the power level of the UV light 122 is at least 10 mW/cm$^2$ at a distance of 0.5 meters, while another, lower-power, disinfection device 100 with operating instructions indicating that a surface to be disinfected by the UV light 122 should be kept in place for 30 seconds or more at a distance of 10 cm may have a visible light exposure area 134 that shows where the power level of the UV light 122 is at least 1 mW/cm$^2$ at a distance of 10 cm.

The lighting module 110 also includes circuitry 140 that actives the second device 130 while the first device 120 is on. The circuitry 140 may be as simple as a conductor 142 to connect the power source of the first device 120 to the second device 130. In other embodiments, the circuitry 140 includes a modulator for the second device 130 that modulates the visible light 132 while the second device 130 is activated to warn that the UV light 122 is being emitted. Any type of circuitry may be used for the modulator, but a astable multivibrator circuit may be used in some embodiments to control a driver for the second device 130 to cause the second device 130 to blink on and off. The modulation may help attract the attention of an observer and further indicate that hazardous UV light 122 is present. Any type of modulation may be used, but in some embodiments the modulation of the visible light 132 includes pulsing or blinking at a rate of between 0.1 and 10 Hertz (Hz) or at a rate of between 1 and 5 Hz. If the modulation turns off (or significantly dims) the second device 130 while it is active, the off-time should be kept short to avoid an observer missing the visible light 132, such as keeping it off for less than 1 second, or even less than one half or one quarter of a second.

In some embodiments, the disinfection device 100 may also include an audio transducer 150, such as a loudspeaker, a piezo-electric chime, or an electromechanical buzzer, and circuitry 140 (integrated with or separate from the modulator) that activates the audio transducer 150 to emit a sound while the first device 120 is activated to warn that the UV light 122 is being emitted. The sound may further enhance the warning to an observer that UV light 122 is present.

A lighting module 110 may include a connector 111 that may mate with another connector (not shown) of the disinfection device 100. The connector 111 includes any number of contacts, depending on the embodiment, including a first contact 112 and a second contact 114 that may together be used to provide power to the lighting module 110 from the disinfection device 100. Alternating current (AC) or direct current (DC) power at any appropriate voltage and current may be provided, depending on the embodiment of the lighting module 110. Note that the first device 120 and the second device 130 are coupled to the first contact 112 as noted by the ground symbols. Although FIG. 1 shows the first contact 112 connected to a ground symbol, this simply represents a connection to other ground symbols in the lighting module 110 and may not be at a ground potential in many embodiments. In this embodiment, the first device 120 is directly connected to both the first contact 112, and the second contact 114, but other embodiments may couple the first device 120 to any number of contacts in the connector 111 directly or through other components, such as a power supply which converts power received from the connector 111 into the type of power needed by the first device 120. The second device 130 is coupled to the second contact 114 through circuitry 140, but in other embodiments, the second device 130 may be directly connected to the second contact 114 or coupled to another contact on the connector 111 that is different than the contact 114 used to provide power to the first device 120. This allows power with different characteristics, such as a different voltage or DC vs AC power to be provided to the second device 130 than is provided to the first device 120. Providing separate power contacts for the devices 120, 130 may move control of the second device 130 into the disinfection device 100 instead of having the control in the lighting module 110, so that the disinfection device 100 is responsible to ensure that the second device 130 is active whenever the first device 120 is on.

The lighting module 110 may be of any size or shape. It may be a component to be used in a light fixture or disinfection device 100 or it may be designed as a stand-alone luminaire to be directly installed into a building or other structure. In some embodiments, the lighting module 110 may be designed to be substantially the same size and shape as traditional light bulb, such as one listed below, and have a traditional lamp base, such as one listed below. One type of traditional light bulb is a standard incandescent light bulb. Although there are far too many standard incandescent bulb sizes and shapes to list here, such standard incandescent light bulbs include, but are not limited to, "A" type bulbous shaped general illumination bulbs such as an A19 or A21 bulb with an E26 or E27, or other sizes of Edison bases, decorative type candle (B), twisted candle, bent-tip candle (CA & BA), fancy round (P) and globe (G) type bulbs with various types of bases including Edison bases of various sizes and bayonet type bases. Other traditional types of traditional light bulbs include reflector (R), flood (FL), elliptical reflector (ER) and Parabolic aluminized reflector (PAR) type bulbs, including but not limited to PAR30 and PAR38 bulbs with E26, E27, or other sizes of Edison bases. Other types of traditional light bulbs include those used in an automobile application, many of which utilize some type of bayonet base. Other traditional light bulbs are halogen bulbs with bi-pin or other types of bases and various different shapes. Another class of traditional light bulbs are fluorescent tube bulbs such as T2, T4, T5, T8 or T10 type tubes with bi-pin, single pin, quad pin, or recessed double contact bases.

In some cases the lighting module 110 may be designed for new applications and may have a new and unique size, shape and electrical connection. In some embodiments, the size and shape of the bulb or its connector may be compliant with a Zhaga specification (or Book to use the Zhaga's terminology) available from the Zhaga Consortium (www.zhagastandard.org). In yet additional embodiments, the lighting module 110 may be an LED strip light as described in the following paragraphs. While an GUV LED strip light may be useful for disinfecting surfaces, it may also be useful for upper-room air disinfection due to its distributed area of UV light emission and inherent directionality based on the orientation of the underlying substrate.

The lighting module 110 may include a multi-die package housing a UV LED die acting as the first device 120 and a visible light LED die acting as the second device 130 mounted on a front side of a substrate of the multi-die package with the connector 111 of the multi-die package providing solder connections to mount the multi-die package in a system, such as the disinfection device 100. The connector 111 of the multi-die package may be provided by two or more solder pads located on a back side of the substrate to act as the first contact 112 and the second contact 114 or in other embodiments, the connector 111 of the multi-die package may be provided by leads extending out from sides of the substrate, such as gull-wing leads or J-leads. Other embodiments of the connector 111 are also contemplated for the multi-die package and are within the scope of this disclosure. The multi-die package may also include circuitry 140 to activate the visible light LED die and may, in some embodiments, modulate the visible light 132 emitted by the visible light LED.

Figure 2A:
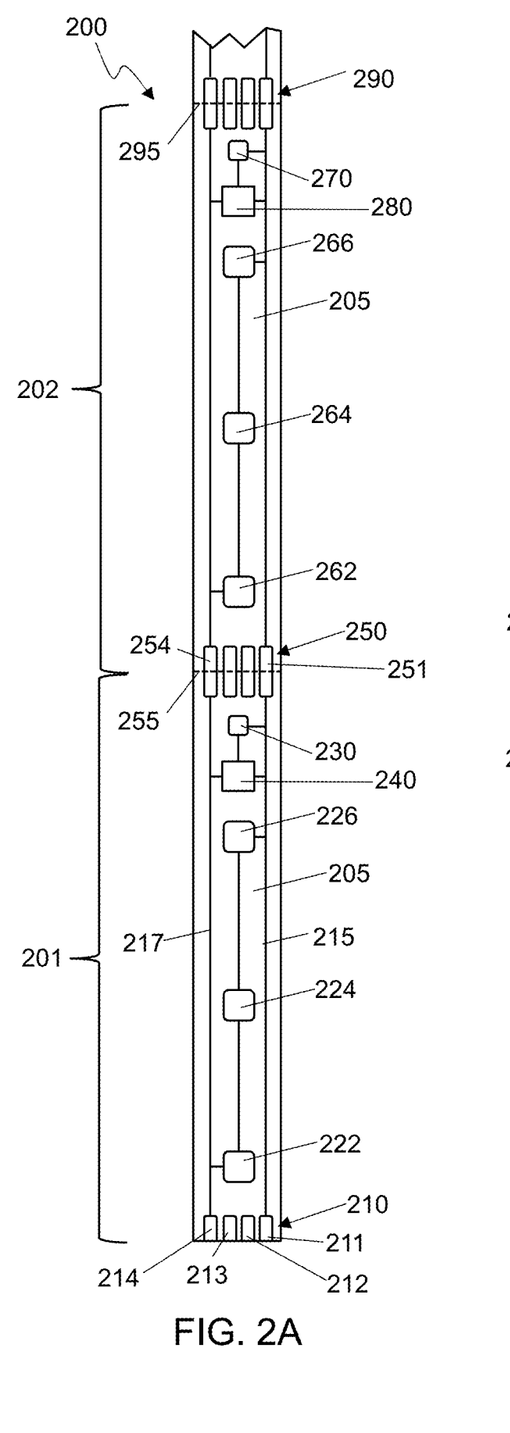
FIG. 2A is a depiction of an embodiment of an LED strip light with both UV-C LEDs and visible light LEDs.
Figure 2B:
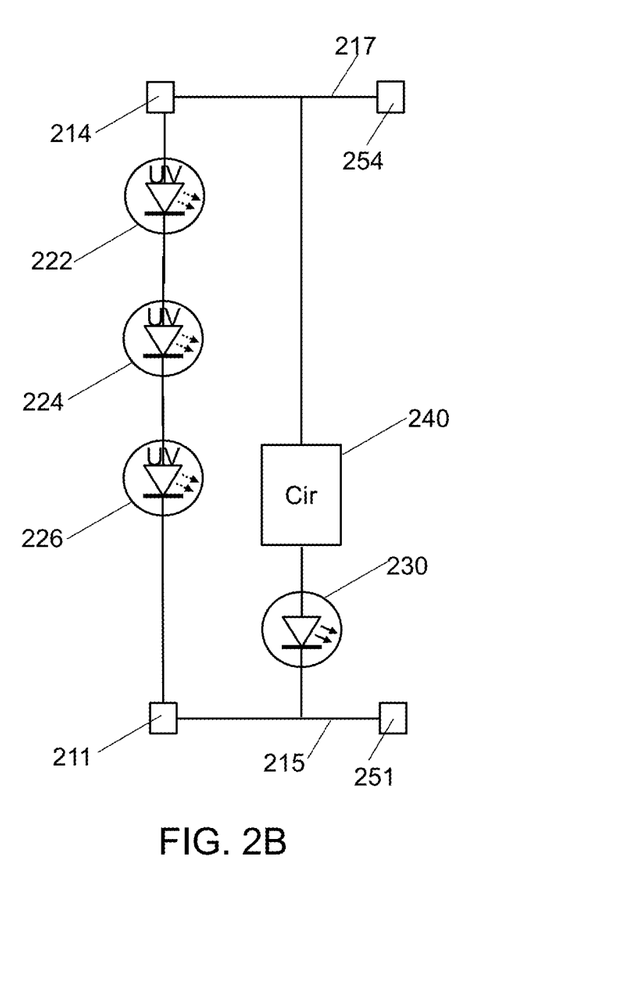
FIG. 2B is a schematic of a section of the LED strip light of FIG. 2A.

FIG. 2A is a depiction of an embodiment of an LED strip light 200 with both UV-C LEDs 222-226, 262-266 and visible light LEDs 230, 270 while FIG. 2B is a schematic of a section 201 of the LED strip light 200 of FIG. 2A which may be replicated for each section of the LED strip light 200. The LED strip light 200 includes an elongated substantially flat substrate 205 having a first set of conductive pads 210 arranged sequentially in a direction perpendicular to an elongation of the substrate 205. The elongation of the substrate is the direction of the longest dimension of the substrate so the first set of conductive pads 210 are arranged at different intervals from the long edge of the substrate 205 along a virtual line perpendicular to its edge. The first set of conductive pads 110 may be located at one end of the substrate 205 and can include two or more conductive pads, including at least a first conductive pad 211 and a second conductive pad 214. The embodiment shown also includes a third conductive pad 212 and a fourth conductive pad 213.

The LED strip light 200 also includes a first light emitting diode (LED) 222 that emits ultraviolet (UV) light in a first wavelength range of 200-315 nm and substantially no light at a wavelength greater than 550 nm. The first LED 222 may emit light in a wavelength subrange of 241-288 nm or 259-270 nm. The first LED 222 is mounted on the substrate 205 and coupled to the first conductive pad 211. In the embodiment shown, two additional UV LEDs 224, 226 are also mounted on the substrate 205 and serially coupled with the first LED 222 with the anode of the first LED 222 connected to the second conductive pad 214, the cathode of the first LED 222 connected to the anode of LED 224, the cathode of LED 224 connected to the anode of LED 226, and the cathode of LED 226 connected to the first conductive pad 211. Using an 8 V forward voltage for the UV LEDs (consistent with the KL265-50V-SM-WD UV-C LED), the LED strip light 200 is configured to operate with 24 VDC power provided at the second conductive pad 214 with the return path through the first conductive pad 211.

The LED strip light 200 also includes a second LED 230 that emits visible light in a second wavelength range of 565-750 nm, although other embodiments may emit any wavelength of visible light. The second LED 230 is mounted on the substrate 205 and coupled to the first conductive pad 211 through its cathode. The LED strip light 200 may also include circuitry 240, mounted on the substrate 205 and coupled to the anode of the second LED 230, that activates the second LED 230 whenever the first LED 222 is on, to provide a visible warning that UV light is present. In some embodiments, the circuitry 240 is coupled to the second conductive pad 214, which is the same conductive pad 214 that provides power to the UV LEDs 222-226, to regulate power received from the second conductive pad 214 to have the proper voltage and/or current for the second LED 230, such as 100 mA at 2.1 V for a typical high-brightness orange-red LED having a peak emission at 625 nm. Thus in some embodiments, both the first LED 222 and the second LED 230 are coupled to the second conductive pad and configured to receive power from the second conductive pad 214, although in the embodiment shown, the second LED 230 is coupled to the second conductive pad 214 through the circuitry 240. Furthermore, the first LED 222 and the second LED 230 are coupled in parallel between the first conductive pad 211 and the second conductive pad 214 and configured to activate the second LED 230 whenever the first LED 222 is powered.

In some embodiments, the circuitry 240 may also control the second LED 230 to modulate the visible light emitted by the second LED 230 while the first LED 222 is powered to warn that the UV light is being emitted. Any modulation may be used to enhance the warning provided by the visible light, including, but not limited to, pulsing or blinking at a rate of between 0.1 and 10 Hz or at a rate between 1 and 5 Hz. In some embodiments, a strobe effect may be used to modulate the visible light, pulsing the second LED 222 very brightly at an interval such as, but not limited to, turning on the second LED 222 for 50 milli-seconds (ms) every 200 ms so that the second LED flashes brightly at a 5 Hz rate.

The LED strip light 200 may include 1, 2, 3, or any number of sections. Each individual section of the LED strip light 200 may be a copy of another section, although some embodiments may include different configurations of LEDs in different sections. In a multi-section LED strip light, the elongated substrate 205 includes a first section 201 and a second section 202 separated by a virtual dividing line 255 perpendicular to the elongation of the substrate. The first section 201 of the elongated substrate 205 has been described above and includes the first set of conductive pads 210 with the first LED 222 and the second LED 230 mounted to the first section 201 of the elongated substrate 205.

A second set of conductive pads 250 is situated on the second section 202 of the elongated substrate 205 arranged sequentially along the virtual dividing line 255. In the embodiment shown, the second set of conductive pads 250 is connected to a mirrored set of conductive pads on the first section of the substrate 205 immediately across the virtual dividing line 255. The second set of conductive pads 250 includes at least a third conductive pad 251 electrically connected to the first conductive pad 211 by a first conductor 215 of the first section 201 of the elongated substrate 205 and a fourth conductive pad 254 electrically connected to the second conductive pad 214 by a second conductor 217 of the first section 201 of the elongated substrate 205.

The LED strip light 200 also includes a third LED 262 that emits UV light in the first wavelength range and a fourth LED 270 that emits visible light in the second wavelength range that are both are mounted to the second section 202 of the elongated substrate 205. The third LED 262 is serially coupled with additional UV LEDs 264, 266 between the third conductive pad 251 and the fourth conductive pad 254. The fourth LED 270 is coupled to the third conductive pad 251 and is driven by circuitry 280 which is connected to the fourth conductive pad 254.

The elongated substrate 205 is configured so that the LED strip light 200 is divisible into two independently operable portions by cutting the elongated substrate 200 at the virtual dividing line 255, yet is operable as a single device with two simultaneously active sections before being cut. So if the uncut substrate is connected to an appropriate power supply, such as a 24 VDC power supply at 1.5 A, through the first set of conductive pads 210, all six UV LEDs 222-226, 262-266 turn on and provide UV light and both visible light LEDs 230, 270 are made active by their respective circuitry 240, 280. But if the LED strip light 200 is cut at the virtual dividing line, either section 201, 202 may be connected to the power supply through its respective set of conductive pads 210, 250 and operate independently of the other. In some embodiments, additional conductors may transmit signals from the circuitry 240 on the first section of the substrate 205 to the circuitry 280 on the second section of the substrate to synchronize the modulation of the visible light LEDs 230, 270, such as a conductor connected between a synchronization output of the circuitry 240 mounted on the first section 201 of the substrate 205 and a synchronization input of the circuitry 280 mounted on the second section 202 of the substrate 205.

Figure 3A:
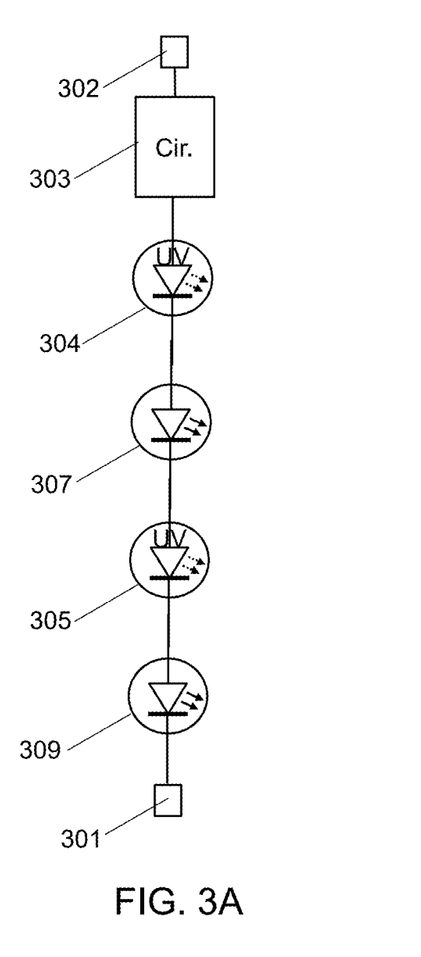
FIGS. 3A, 3B, and 3C are schematics of alternative embodiments of a section of an LED strip light.
Figure 3B:
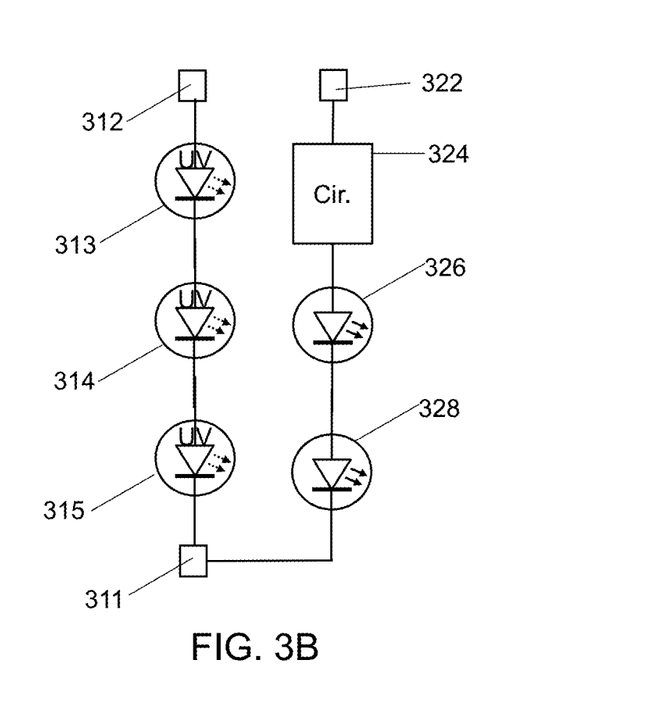
Figure 3C:
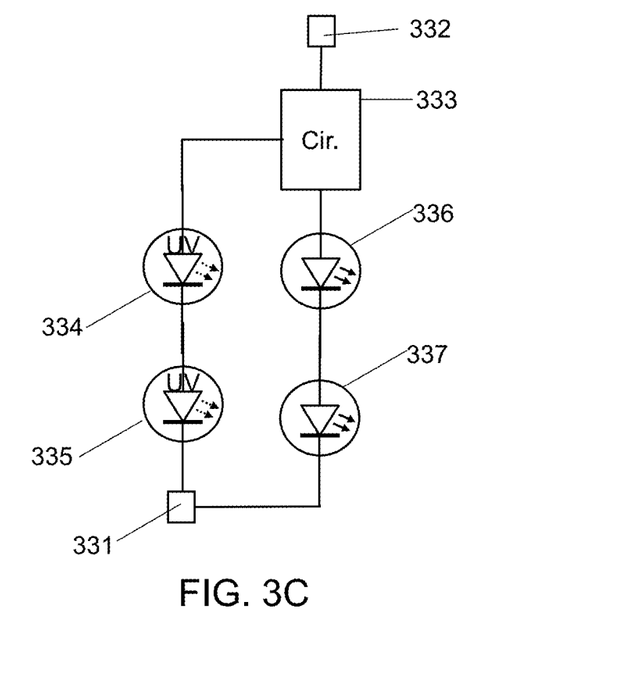

FIGS. 3A, 3B, and 3C are schematics of alternative embodiments of a section of an LED strip light as compared to the embodiment of FIG. 2B. FIG. 3A shows an alternative embodiment of an LED strip light having a single serially coupled chain of a mix of UV LEDs 304, 305 and visible light LEDs 307, 309 serially coupled with circuitry 303 which may regulate the power received at conductive pad 302 as appropriate. The specific embodiment shown has a power input of the circuitry 303 connected to the second conductive pad 302 and an output of the circuitry 303 connected to an anode of UV LED 304. A cathode of the UV LED 304 is connected to an anode of visible light LED 307 and a cathode of the visible light LED 307 is connected to an anode of UV LED 305. A cathode of the UV LED 305 is connected to an anode of visible light LED 309 and a cathode of the visible light LED 309 is connected to the first conductive pad 301. Thus, the first (UV) LED 304 and the second (visible light) LED 307 are serially coupled between the first conductive pad 301 and the second conductive pad 302. The LED strip light of FIG. 3A also includes one or more additional LEDs 305, 309 serially coupled with the first LED 304 and the second LED 307 between the first conductive pad 301 and the second conductive pad 302, where the one or more additional LEDs 305, 307 are each respectively emitting light in either the first wavelength range (UV) or the second wavelength range (visible light).

FIG. 3B shows an alternative embodiment of an LED strip light where the first (UV) LED 301 is coupled between the first conductive pad 311 and the second conductive pad 312 and the second (visible light) LED 326 is coupled between the first conductive pad 311 and a third conductive pad 322 of the first set of conductive pads which includes the first conductive pad 311 and the second conductive pad 312. Specifically looking at the embodiment of FIG. 3B, the first conductive pad 311 is connected to a cathode of UV LED 315 and a cathode of visible light LED 328. An anode of the UV LED 315 is connected to a cathode of UV LED 314, an anode of the UV LED 314 is connected to a cathode of UV LED 313, and an anode of UV LED 313 is connected to the second conductive pad 312. An anode of the visible light LED 328 is connected to a cathode of visible light LED 326 with an anode of the visible light LED 326 connected to circuitry 324 which receives power through the third conductive pad 322 allowing for independent powering of the visible light LEDs 326, 328 from the UV LEDs 313-315. The circuitry 324 may be simple conductors connecting pad 322 to LED 326, power regulation circuitry, modulation circuitry, or a combination of power regulation and modulation, depending on the embodiment.

FIG. 3C shows an alternative embodiment of an LED strip light where the first (UV) LED 334 and the second (visible light) LED 336 are coupled in parallel between the first conductive pad 331 and the second conductive pad 332. This embodiment is configured to activate the second LED 336 whenever the first LED 334 is powered. One or more additional UV LEDs 335 are serially coupled with the first LED 334 between the first conductive pad 331 and the second conductive pad 332 to form a first set of LEDs and one or more additional visible light LEDs 337 are serially coupled with the second LED 336 between the first conductive pad 331 and the second conductive pad 332 to form a second set of LEDs in parallel to the first set of LEDs between the first conductive pad 331 and the second conductive pad 332. The circuitry 333 may be simple conductors connecting pad 332 to the anodes of UV LED 334 and visible light LED 336, power regulation circuitry, modulation circuitry, or a combination of power regulation and modulation, depending on the embodiment.

As FIGS. 2B, 3A, 3B, and 3C show, a wide variety of configurations of UV LEDs and visible light LEDs are possible in each section of the LED strip light. Different configurations may be selected to match various voltage and drive characteristics of a power supply and/or UV light and visible light requirements for a particular embodiment. In some embodiments of an LED strip light, each section has an identical configuration of UV LEDs, visible light LEDs, and circuitry.

Figure 4:
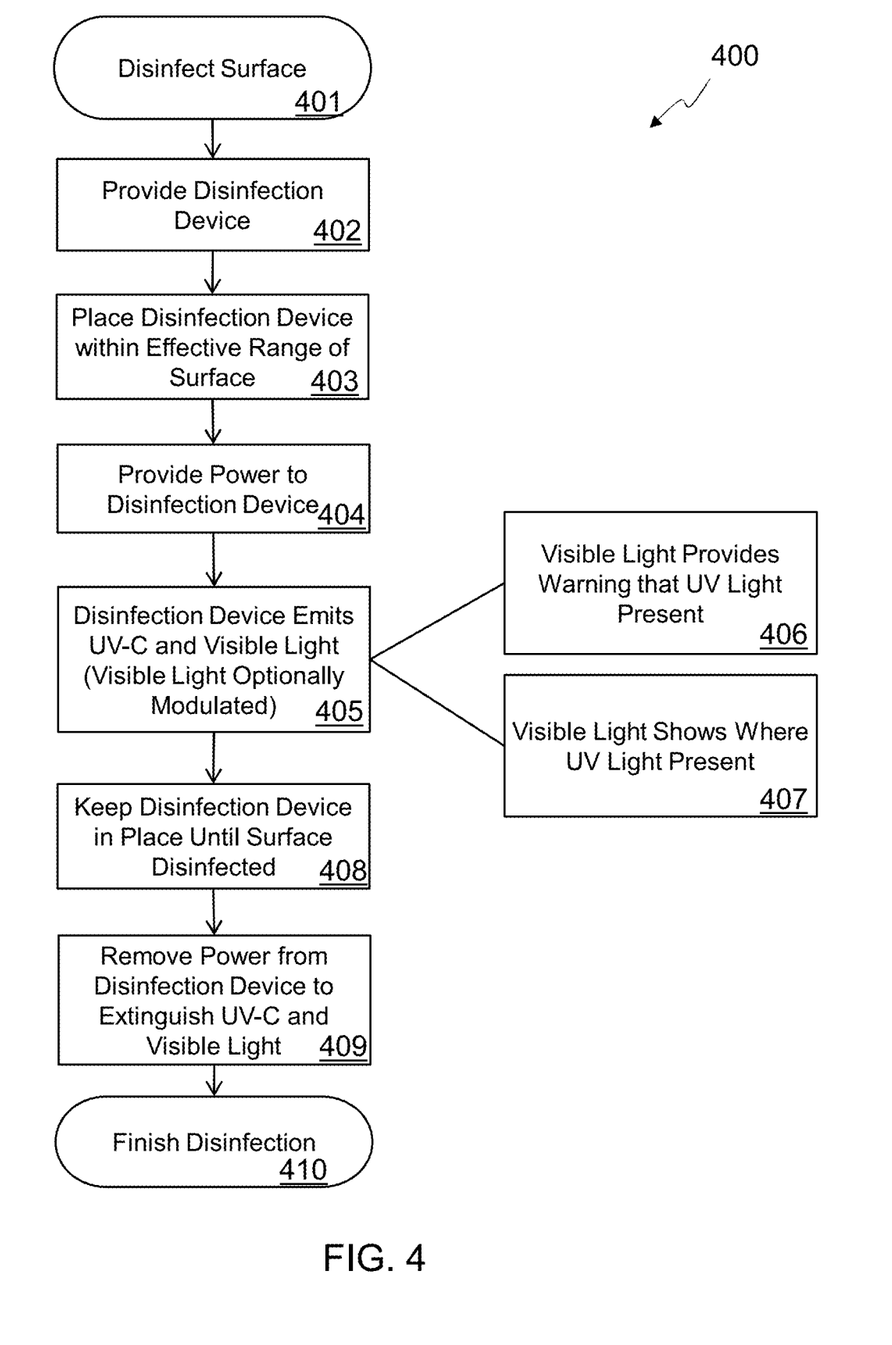
FIG. 4 is a flowchart of an embodiment of a method for disinfecting a surface.

FIG. 4 is a flowchart 400 of an embodiment of a method for disinfecting a surface 99 using the disinfection device 100 as shown in FIG. 1. The surface to be disinfected may be a surface 99 of an operating room that is suspected of being contaminated with the SARS-CoV-2 virus. The method 400 starts 401 with providing 402 the disinfection device 100. The disinfection device 100 is placed 403 within an effective range of the surface 99 to be disinfected and power is provided 404 to the disinfection device 100 to turn on the first device 120 and activate the second device 130. Power may be provided by turning on a switch of the disinfection device 100, plugging in the disinfection device 100, or by any other technique as appropriate for the disinfection device 100. Once power is provided to the disinfection device 100, it emits 405 UV-C 122 and visible light 132, which may be modulated in some embodiments. The visible light may provide 406 a warning to an individual that UV light 122 is being emitted and/or may show 407 where the UV light 122 is present. The disinfection device 100 is kept 408 in place until the surface 99 is disinfected and then power may be removed 409 from the disinfection device to extinguish the UV-C 122 and visible light 132 to finish 410 the disinfection process.

Examples of various embodiments are described in the following paragraphs:

Embodiment 1. A disinfection device comprising: a first device that emits ultraviolet (UV) light in a first wavelength range of 200-315 nanometers (nm) and substantially no light at a wavelength greater than 550 nm; a second device that emits visible light in a second wavelength range of 565-750 nm; and circuitry that actives the second device while the first device is on.

Embodiment 2. The disinfection device of embodiment 1, the first device emitting the UV light at a power level sufficient to deactivate at least 90% of SARS-CoV-2 virus on a surface of a medical device within one second at a distance of 0.5 meters or greater.

Embodiment 3. The disinfection device of embodiment 1 or 2, the first device emits the UV light at a power level of at least 10 mW/cm2 at a distance of 0.5 meters for at least one area within an exposure pattern for the UV light from the disinfection device.

Embodiment 4. The disinfection device of any of embodiments 1 through 3, wherein the first device is mounted within the disinfection device to have a first exposure pattern for the UV light and the second device is mounted within the disinfection device to have a second exposure pattern for the visible light that completely covers the first exposure pattern.

Embodiment 5. The disinfection device of any of embodiments 1 through 3, wherein the first device is mounted within the disinfection device to have a first exposure pattern for the UV light and the second device is mounted within the disinfection device to have a second exposure pattern for the visible light that is substantially the same as the first exposure pattern.

Embodiment 6. The disinfection device of any of embodiments 1 through 3, wherein the first device is mounted within the disinfection device to have a first exposure pattern for the UV light and the second device is mounted within the disinfection device to have a second exposure pattern for the visible light that is a subset of the first exposure pattern and shows an area where a power level of the UV light is germicidally effective.

Embodiment 7. The disinfection device of any of embodiments 1 through 6, wherein the first device emits substantially no light at a wavelength greater than 380 nm.

Embodiment 8. The disinfection device of any of embodiments 1 through 7, wherein the UV light has a peak emission in a wavelength subrange of 241-288 nm.

Embodiment 9. The disinfection device of any of embodiments 1 through 7, the first device comprising a light emitting diode (LED) having a peak emission in a wavelength subrange of 259-270 nm.

Embodiment 10. The disinfection device of any of embodiments 1 through 9, wherein the visible light is bright enough to encourage an observer to look away from the disinfection device.

Embodiment 11. The disinfection device of any of embodiments 1 through 10, the second device comprising a light emitting diode (LED).

Embodiment 12. The disinfection device of any of embodiments 1 through 11, the circuitry that actives the second device comprising one or more conductors that electrically connect a power source of the disinfection device to a power input of the first device and a power input of the second device.

Embodiment 13. The disinfection device of any of embodiments 1 through 12, the circuitry that actives the second device comprising an elongated substantially flat substrate having a first set of conductive pads arranged sequentially in a direction perpendicular to an elongation of the substrate, the first set of conductive pads including at least a first conductive pad and a second conductive pad; the first device comprising an LED mounted on the substrate and electrically coupled between the first conductive pad and the second conductive pad; and the second device comprising an LED mounted on the substrate and electrically coupled to at least the first conductive pad.

Embodiment 14. The disinfection device of any of embodiments 1 through 13, the circuitry that actives the second device comprising a modulator for the second device that modulates the visible light while the second device is activated to warn that the UV light is being emitted.

Embodiment 15. The disinfection device of any of embodiments 1 through 14, wherein the modulation of the visible light comprises a pulsing or blinking at a rate of between 0.1 and 10 Hz.

Embodiment 16. The disinfection device of any of embodiments 1 through 14, wherein the modulation of the visible light comprises a pulsing or blinking at a rate of between 1 and 5 Hz.

Embodiment 17. The disinfection device of any of embodiments 1 through 16, further comprising: an audio transducer; and circuitry that activates the audio transducer to emit a sound while the first device is activated to warn that the UV light is being emitted.

Embodiment 18. A method for disinfecting a surface, the method comprising: providing the disinfection device of embodiment 1; placing the disinfection device within an effective range of the surface to be disinfected; providing power to the disinfection device to turn on the first device and activate the second device; wherein the visible light provides a warning to an individual that UV light is being emitted.

Embodiment 19. The method of embodiment 18, wherein the surface to be disinfected is a surface of an operating room that is suspected of being contaminated with the SARS-CoV-2 virus.

Embodiment 20. A lighting module comprising: a connector that includes a first contact and a second contact; a first device that emits ultraviolet (UV) light in a first wavelength range of 200-315 nm and substantially no light at a wavelength greater than 550 nm, the first device coupled to the first contact; and a second device that emits visible light in a second wavelength range of 400-750 nm, the second device coupled to the first contact.

Embodiment 21. The lighting module of embodiment 20, wherein the second device has a peak emission in a wavelength subrange of 565-750 nm to emit yellow, orange, or red visible light to indicate a hazardous condition.

Embodiment 22. The lighting module of embodiment 20 or 21, wherein the first device emits substantially no light having a greater than 380 nm wavelength.

Embodiment 23. The lighting module of any of embodiments 20 through 22, wherein the lighting module comprises an LED strip light.

Embodiment 24. The lighting module of any of embodiments 20 through 23, further comprising: an elongated substantially flat substrate having a first set of conductive pads arranged sequentially in a direction perpendicular to an elongation of the substrate to form the connector, the first set of conductive pads including at least the first contact and the second contact; the first device comprising a first light emitting diode (LED) mounted on the substrate; and the second device comprising a second LED mounted on the substrate.

Embodiment 25. The lighting module of any of embodiments 20 through 24, further comprising: a substrate; a UV LED die comprising the first device; and a visible light LED die comprising the second device; the UV LED die and the visible light LED die both mounted on a front side of the substrate.

Embodiment 26. The lighting module of embodiment 25, comprising a multi-die package including the substrate, the first contact, and the second contact.

Embodiment 27. The lighting module of embodiment 25 or 26, wherein the first contact and the second contact are located on a back side of the substrate.

Embodiment 28. The lighting module of embodiment 25 or 26, wherein the first contact and the second contact respectively comprise a first lead and a second lead extending out from sides of the substrate.

Embodiment 29. The lighting module of any of embodiments 20 through 22, wherein the connector is compliant with a Zhaga specification.

Embodiment 30. The lighting module of any of embodiments 20 through 22, wherein the lighting module is substantially the same size and shape as a traditional light bulb and the connector comprises a traditional lamp base.

Embodiment 31. An apparatus comprising: an elongated substantially flat substrate having a first set of conductive pads arranged sequentially in a direction perpendicular to an elongation of the substrate, the first set of conductive pads including at least a first conductive pad and a second conductive pad; a first light emitting diode (LED) that emits ultraviolet (UV) light in a first wavelength range of 200-315 nm and substantially no light at a wavelength greater than 380 nm, the first LED mounted on the substrate and coupled to the first conductive pad; and a second LED that emits visible light in a second wavelength range of 400-750 nm, the second LED mounted on the substrate and coupled to the first conductive pad.

Embodiment 32. The apparatus of embodiment 31, wherein the second LED has a peak emission in a wavelength subrange of 565-750 nm.

Embodiment 33. The apparatus of embodiment 31 or 32, the first LED having a peak emission in a wavelength subrange of 259-270 nm.

Embodiment 34. The apparatus of any of embodiments 31 through 33, wherein first LED and the second LED are both also coupled to the second conductive pad and configured to receive power from the second conductive pad.

Embodiment 35. The apparatus of any of embodiments 31 through 34, wherein first LED and the second LED are coupled in parallel between the first conductive pad and the second conductive pad and configured to activate the second LED whenever the first LED is powered.

Embodiment 36. The apparatus of any of embodiments 31 through 34, wherein first LED and the second LED are serially coupled between the first conductive pad and the second conductive pad.

Embodiment 37. The apparatus of embodiment 36, further comprising one or more additional LEDs serially coupled with the first LED and the second LED between the first conductive pad and the second conductive pad, the one or more additional LEDs each respectively emitting light in either the first wavelength range or the second wavelength range.

Embodiment 38. The apparatus of any of embodiments 31 through 33, wherein first LED is coupled between the first conductive pad and the second conductive pad and the second LED is coupled between the first conductive pad and a third conductive pad of the first set of conductive pads.

Embodiment 39. The apparatus of any of embodiments 31 through 38, further comprising circuitry mounted on the substrate and coupled to the second LED to modulate the visible light emitted by the second LED while the first LED is powered to indicate that the UV light is being emitted.

Embodiment 40. The apparatus of embodiment 39, wherein the modulation of the visible light comprises a pulsing or blinking at a rate of between 0.1 and 10 Hz.

Embodiment 41. The apparatus of embodiment 39, wherein the modulation of the visible light comprises a pulsing or blinking at a rate of between 1 and 5 Hz.

Embodiment 42. The apparatus of any of embodiments 39 through 41, wherein the circuitry is configured to receive power from the second conductive pad.

Embodiment 43. The apparatus of any of embodiments 31 through 42, further comprising: one or more additional UV LEDs that emit light in the first wavelength range serially coupled with the first LED between the first conductive pad and the second conductive pad to form a first set of LEDs.

Embodiment 44. The apparatus of any of embodiments 31 through 42, further comprising: one or more additional visible light LEDs that emit light in the second wavelength range serially coupled with the second LED.

Embodiment 45. The apparatus of embodiments 31 through 35, further comprising: one or more additional UV LEDs that emit light in the first wavelength range serially coupled with the first LED between the first conductive pad and the second conductive pad to form a first set of LEDs; and one or more additional visible light LEDs that emit light in the second wavelength range serially coupled with the second LED between the first conductive pad and the second conductive pad to form a second set of LEDs in parallel to the first set of LEDs between the first conductive pad and the second conductive pad.

Embodiment 46. The apparatus of embodiments 31 through 45, wherein the elongated substrate includes a first section and a second section separated by a virtual dividing line perpendicular to the elongation of the substrate, the first section of the elongated substrate including the first set of conductive pads with the first LED and the second LED mounted to the first section of the elongated substrate, the apparatus further comprising: a second set of conductive pads on the second section of the elongated substrate arranged sequentially along the virtual dividing line, the second set of conductive pads including at least a third conductive pad electrically connected to the first conductive pad by a first conductor of the first section of the elongated substrate and a fourth conductive pad electrically connected to the second conductive pad by a second conductor of the first section of the elongated substrate; a third LED that emits UV light in the first wavelength range, the third LED coupled to the third conductive pad and mounted to the second section of the elongated substrate; and a fourth LED that emits visible light in the second wavelength range, the fourth LED coupled to the third conductive pad and mounted to the second section of the elongated substrate; wherein the elongated substrate is configured so that the apparatus is divisible into two independently operable portions by cutting the elongated substrate at the virtual dividing line yet is operable as a single device with two simultaneously active sections before being cut.

Embodiment 47. The apparatus of embodiment 46, further comprising: first modulation circuitry, mounted on the first section of the of the elongated substrate and coupled to the second LED, to modulate the visible light emitted by the second LED; second modulation circuitry, mounted on the second section of the of the elongated substrate and coupled to the fourth LED, to modulate the visible light emitted by the fourth LED; and a conductor connected between a synchronization output of the first modulation circuitry and a synchronization input of the second modulation circuitry.

Unless otherwise indicated, all numbers expressing quantities, properties, measurements, and so forth, used in the specification and claims are to be understood as being modified in all instances by the term "about." The recitation of numerical ranges by endpoints includes all numbers subsumed within that range, including the endpoints (e.g. 1 to 5 includes 1, 2.78, π, 3.33, 4, and 5).

As used in this specification and the appended claims, the singular forms "a", "an", and "the" include plural referents unless the content clearly dictates otherwise. Furthermore, as used in this specification and the appended claims, the term "or" is generally employed in its sense including "and/or" unless the content clearly dictates otherwise. As used herein, the term "coupled" includes direct and indirect connections. Moreover, where first and second devices are coupled, intervening devices including active devices may be located there between.

The description of the various embodiments provided above is illustrative in nature and is not intended to limit this disclosure, its application, or uses. Thus, different variations beyond those described herein are intended to be within the scope of embodiments. Such variations are not to be regarded as a departure from the intended scope of this disclosure. As such, the breadth and scope of the present disclosure should not be limited by the above-described exemplary embodiments, but should be defined only in accordance with the following claims and equivalents thereof.

What is claimed is:

1. A disinfection device comprising:
   an electrical conductor;
   a first device that emits ultraviolet (UV) light in a first wavelength range of 200-315 nanometers (nm) and substantially no light at a wavelength greater than 550 nm, the first device coupled to the electrical conductor;
   a second device that emits visible light in a second wavelength range of 565-750 nm, the second device coupled to the electrical conductor; and
   circuitry that modulates the visible light emitted by the second device at a rate between 0.1 and 10 Hz while the first device is on to warn that the UV light is being emitted.

2. The disinfection device of claim 1, the first device emitting the UV light at a power level sufficient to deactivate at least 90% of SARS-CoV-2 virus on a surface of a medical device within one second at a distance of 0.5 meters or greater.

3. The disinfection device of claim 1, the first device emits the UV light at a power level of at least 10 mW/cm$^2$ at a distance of 0.5 meters for at least one area within an exposure pattern for the UV light from the disinfection device.

4. The disinfection device of claim 1, wherein the first device is mounted within the disinfection device to have a first exposure pattern for the UV light and the second device is mounted within the disinfection device to have a second exposure pattern for the visible light that is a subset of the first exposure pattern and shows an area where a power level of the UV light is germicidally effective.

5. The disinfection device of claim 1, further comprising:
   an audio transducer; and
   additional circuitry that activates the audio transducer to emit a sound while the first device is activated to further warn that the UV light is being emitted.

6. The disinfection device of claim 1, wherein the first device is mounted within the disinfection device to have a first exposure pattern for the UV light and the second device is mounted within the disinfection device to have a second exposure pattern for the visible light that overlaps with at least a portion of the first exposure pattern.

7. A lighting module comprising:
   an electrical conductor;
   a first device that emits ultraviolet (UV) light in a first wavelength range of 200-315 nm and substantially no light at a wavelength greater than 550 nm, the first device coupled to the electrical conductor;

a second device that emits visible light in a second wavelength range of 400-750 nm, the second device coupled to the electrical conductor; and circuitry coupled to the second device to modulate the visible light emitted by the second device at a rate between 0.1 and 10 Hz.

8. The lighting module of claim 7, wherein the second device has a peak emission in a wavelength subrange of 565-750 nm.

9. The lighting module of claim 7, wherein the first device emits substantially no light having a wavelength greater than 380 nm.

10. The lighting module of claim 7, further comprising:
a connector that includes a first electrical contact and a second electrical contact, the first electrical contact electrically connected to the electrical conductor.

11. The lighting module of claim 7, further comprising:
a substrate;
a UV LED die comprising the first device; and
a visible light LED die comprising the second device;
the UV LED die and the visible light LED die both mounted on a front side of the substrate.

12. The lighting module of claim 7, wherein the lighting module comprises an LED strip light.

13. The lighting module of claim 10, wherein the connector is compliant with a Zhaga specification.

14. The lighting module of claim 7, wherein the first device is mounted within the lighting module to have a first exposure pattern for the UV light and the second device is mounted within the lighting module to have a second exposure pattern for the visible light that overlaps with at least a portion of the first exposure pattern.

15. An apparatus comprising:
an elongated substantially flat substrate having a first set of conductive pads arranged sequentially in a direction perpendicular to an elongation of the substrate, the first set of conductive pads including at least a first conductive pad and a second conductive pad, wherein the first conductive pad comprises an electrical conductor;
a first light emitting diode (LED) that emits ultraviolet (UV) light in a first wavelength range of 200-315 nm and substantially no light at a wavelength greater than 380 nm, the first LED mounted on the substrate and coupled to the first conductive pad;
a second LED that emits visible light in a second wavelength range of 400-750 nm, the second LED mounted on the substrate and coupled to the first conductive pad; and
modulation circuitry mounted on the substrate and coupled to the second LED to modulate the visible light emitted by the second LED at a rate between 0.1 and 10 Hz while the first LED is powered to indicate that the UV light is being emitted.

16. The apparatus of claim 15, wherein the second LED has a peak emission in a wavelength subrange of 565-750 nm.

17. The apparatus of claim 15, the first LED having a peak emission in a wavelength subrange of 259-270 nm.

18. The apparatus of claim 15, wherein first LED and the second LED are both also coupled to the second conductive pad and configured to receive power from the second conductive pad.

19. The apparatus of claim 15, wherein first LED is coupled between the first conductive pad and the second conductive pad and the second LED is coupled between the first conductive pad and a third conductive pad of the first set of conductive pads.

20. The apparatus of claim 15, further comprising:
one or more additional UV LEDs that emit light in the first wavelength range serially coupled with the first LED between the first conductive pad and the second conductive pad to form a first set of LEDs.

21. The apparatus of claim 15, wherein the elongated substrate includes a first section and a second section separated by a virtual dividing line perpendicular to the elongation of the substrate, the first section of the elongated substrate including the first set of conductive pads with the first LED, the second LED, and the modulation circuitry mounted to the first section of the elongated substrate, the apparatus further comprising:
a second set of conductive pads on the second section of the elongated substrate arranged sequentially along the virtual dividing line, the second set of conductive pads including at least a third conductive pad electrically connected to the first conductive pad by a first conductor of the first section of the elongated substrate and a fourth conductive pad electrically connected to the second conductive pad by a second conductor of the first section of the elongated substrate, the first conductor comprising the electrical conductor;
a third LED that emits UV light in the first wavelength range, the third LED coupled to the third conductive pad and mounted to the second section of the elongated substrate;
a fourth LED that emits visible light in the second wavelength range, the fourth LED coupled to the third conductive pad and mounted to the second section of the elongated substrate;
second modulation circuitry, mounted on the second section of the of the elongated substrate and coupled to the fourth LED, to modulate the visible light emitted by the fourth LED at a rate between 0.1 and 10 Hz; and
a third conductor connected between a synchronization output of the modulation circuitry and a synchronization input of the second modulation circuitry;
wherein the elongated substrate is configured so that the apparatus is divisible into two independently operable portions by cutting the elongated substrate at the virtual dividing line yet is operable as a single device with two simultaneously active sections before being cut.

22. The apparatus of claim 15, wherein the first LED is mounted on a first side of the substrate to have a first exposure pattern for the UV light and the second LED is mounted on the first side of the substrate to have a second exposure pattern for the visible light that overlaps with at least a portion of the first exposure pattern.

* * * * *